United States Patent
Cook et al.

[11] Patent Number: 5,470,324
[45] Date of Patent: Nov. 28, 1995

[54] NON-REFLUXING SUCTION CANISTER SYSTEM AND COMPONENTS THEREFOR

[75] Inventors: Charles Cook, Whitehouse, Tex.; Mostafa Zomorodi, Palmdale; Richard C. G. Dark, Rancho Cucomonga, both of Calif.

[73] Assignee: Baxter International Inc., Deerfield, Ill.

[21] Appl. No.: 86,782

[22] Filed: Jul. 1, 1993

[51] Int. Cl.⁶ .................................................. A61M 1/00
[52] U.S. Cl. ........................................... 604/319; 128/760
[58] Field of Search .................................... 604/317–321, 604/323; 251/149.2; 128/760, 768

[56] References Cited

U.S. PATENT DOCUMENTS

| | | |
|---|---|---|
| 3,863,664 | 2/1975 | Holbrook et al. . |
| 3,913,780 | 10/1975 | Holbrook et al. . |
| 3,938,540 | 2/1976 | Holbrook et al. . |
| 4,013,076 | 3/1977 | Puderbaugh et al. . |
| 4,275,732 | 6/1981 | Gereg ............................ 128/DIG. 24 |
| 4,379,455 | 4/1983 | Deaton . |
| 4,384,580 | 5/1983 | Leviton . |
| 4,388,922 | 6/1983 | Telang . |
| 4,397,643 | 8/1983 | Rygiel ................................ 604/317 |
| 4,430,084 | 2/1984 | Deaton ............................... 604/317 |
| 4,465,483 | 8/1984 | Weilbacher . |
| 4,475,904 | 10/1984 | Wang . |
| 4,642,105 | 2/1987 | Toter ................................. 604/323 |
| 4,681,571 | 7/1987 | Nehring ............................. 604/320 |
| 4,772,278 | 9/1988 | Baber ................................. 604/323 |
| 4,877,219 | 10/1989 | Yano ............................... 251/149.2 |
| 5,011,470 | 4/1991 | Kurtz et al. . |
| 5,141,504 | 8/1992 | Herweck ............................ 604/317 |
| 5,149,325 | 9/1992 | Telang et al. . |
| 5,185,007 | 2/1993 | Middaugh ......................... 604/319 |
| 5,318,548 | 7/1994 | Filshie ................................ 604/319 |

FOREIGN PATENT DOCUMENTS 8900424  2/1990  WIPO ................................... 604/319

Primary Examiner—Randall L. Green
Assistant Examiner—Dennis Ruhl
Attorney, Agent, or Firm—Robert A. Stenzel; Kay H. P. Hannafan; Paul C. Flattery

[57] ABSTRACT

A patient fluid collection system is disclosed which includes a fluid collection reservoir, a cover for the reservoir and a liner within the reservoir comprising an enlargeable or expandable wall portion such that the wall portion may expand if the liner fills with fluid. An anti-reflux system is also disclosed as well as a new tandem tube and a new connector.

31 Claims, 8 Drawing Sheets

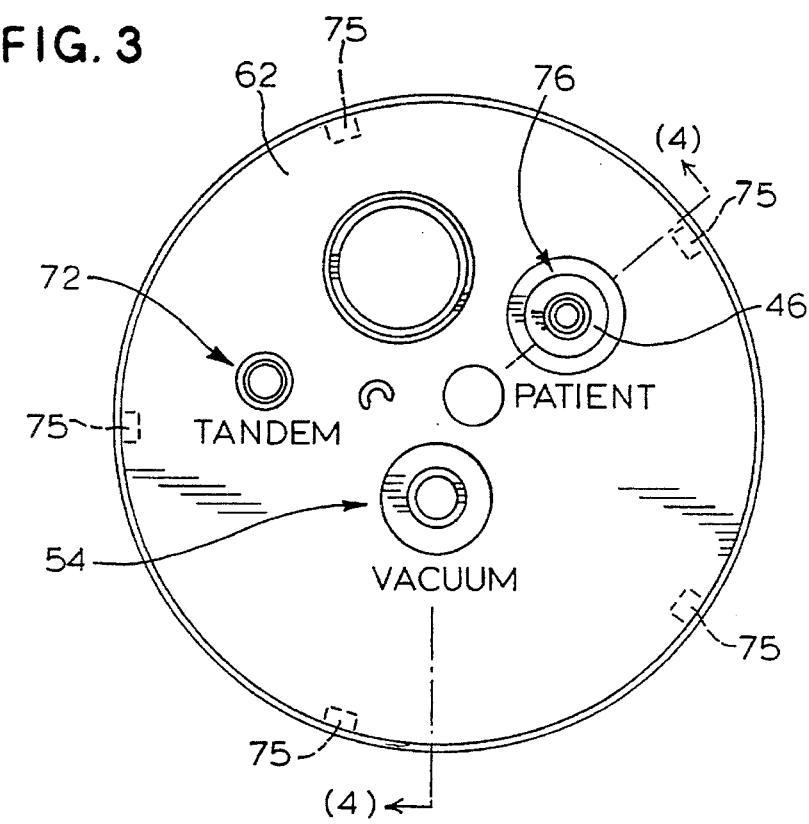
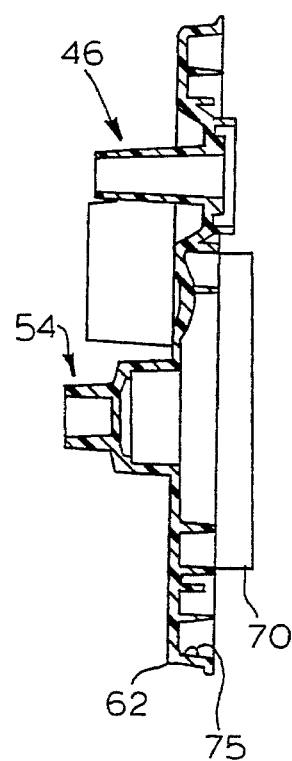
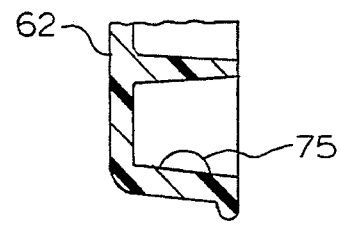
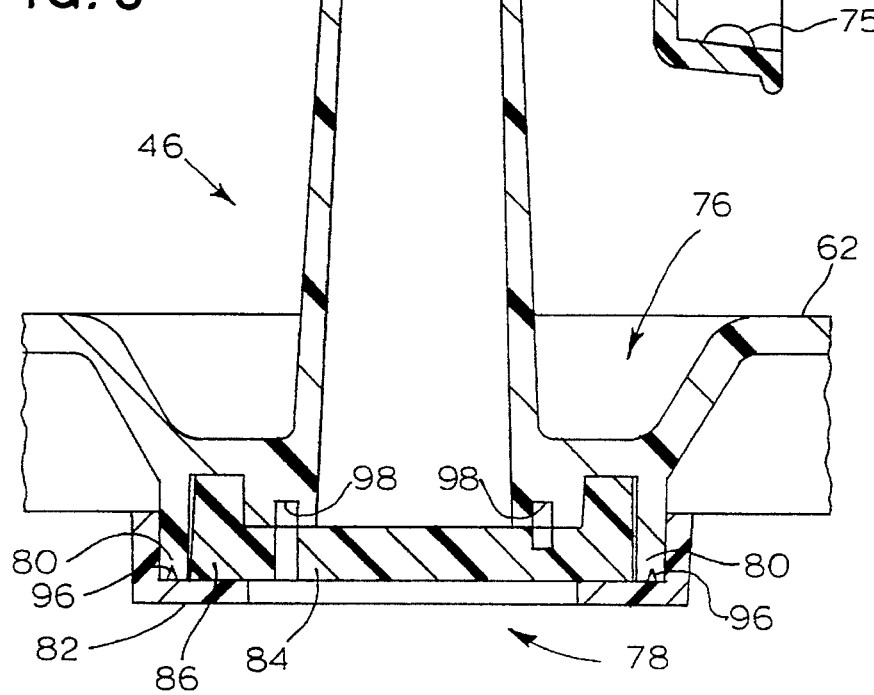

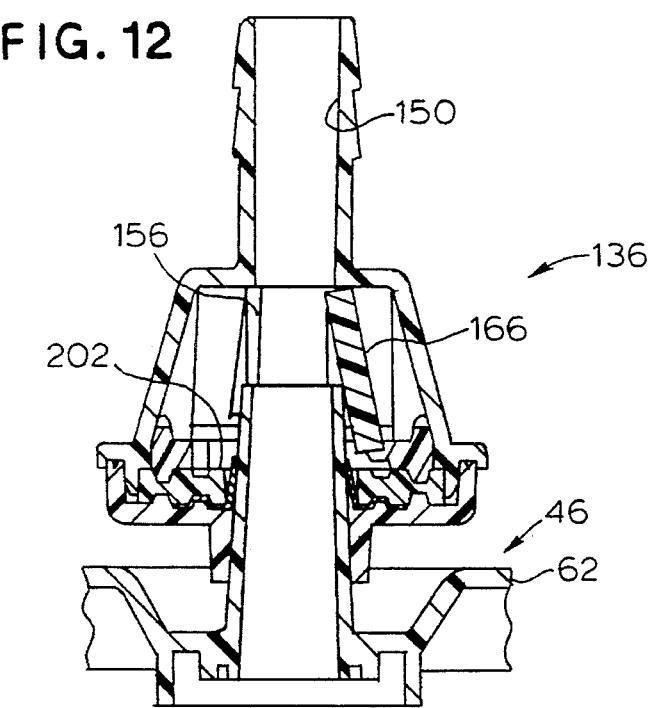
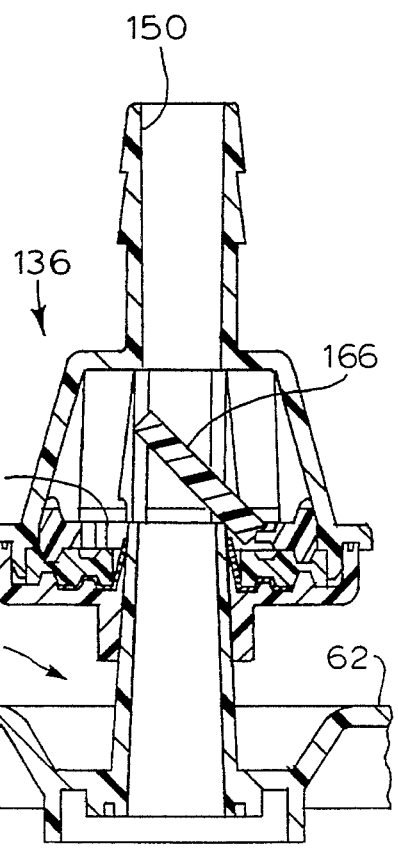
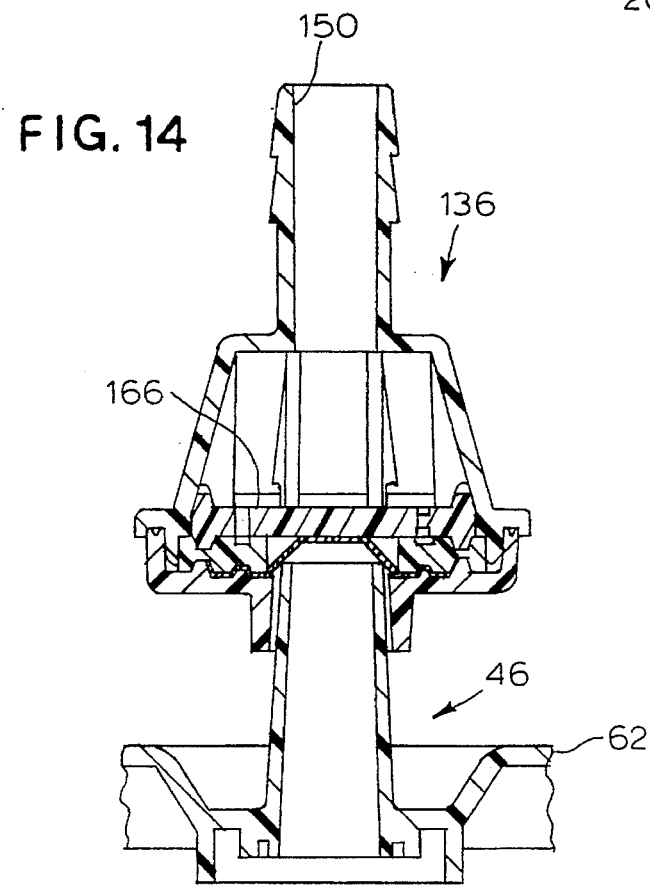

NON-REFLUXING SUCTION CANISTER SYSTEM AND COMPONENTS THEREFOR

BACKGROUND OF THE INVENTION

1. Field of the Invention

The present invention relates to non-refluxing suction canister systems and components therefor, and more specifically to such systems having canisters dosed by antirefluxing valves or which have flexible liners.

2. Related Art

During operative surgery and other medical and biological procedures, suction canister systems are used to collect fluids from a patient, including blood, saline, and any other fluids which may accumulate or must be removed and contained during the procedure and disposed of after the procedure. The collection system uses suction canisters and a vacuum source. While a single canister can be and is often used, a multiple canister suction system will be described because the use and operation of a single canister system is apparent from that for a multiple system. Multiple canisters are arranged in tandem with a first canister having a suction tube to collect fluids from a source and to deposit the fluids in the first canister. Downstream canisters are coupled together with their vacuum sources applied in series or in parallel from a vacuum source connected at the end canister.

Typically, a canister unit includes an open-top cylindrical canister closed by a cover or lid to which is sealed an internal liner to be contained in the canister. Vacuum is applied through the canister wall to the space or cavity between the liner and the canister wall to expand the liner outwardly toward the canister wall. Vacuum is also applied for each canister to a vacuum port in the lid to develop a subatmospheric pressure or vacuum within the liner, which vacuum then also develops at the collection tube at the desired level. Tandem tubes connect the interior of the liner of the first canister to the inlet port on the lid of the next succeeding canister so that when the first canister fills, fluid in the first canister thereafter passes to the second canister, and so on.

The lid typically includes several access ports with associated attachment or connection elements. A vacuum port accepts a tube from the vacuum source to apply vacuum internal to the liner. An inlet or patient port accepts one end of the suction tube. A large access port is typically capped until a fluid setting agent such as Isolizer is to be added. An outlet or "ortho" port includes a wider riser portion than the patient port for connection of a suction tube during orthopaedic operations or for connection of a tandem tube for connecting an additional collection canister to the first. The vacuum port of each canister includes a float valve to prevent withdrawal of fluids into the vacuum system. However, the other ports in the lid which are exposed to the fluids lack any valve and are subject to reflux and may lead to contamination of personnel or a working area.

In situations where one or more canisters become filled before the end of the procedure, fluid may reflux or come out of one or more ports under certain circumstances. For example, if vacuum is removed from the system, the pressure differential between atmosphere on the one hand and the cavity between the canister and the lining on the other, created by the vacuum between the canister and the liner, is removed. Removal of the vacuum allows the liner to collapse somewhat, due to liner elasticity, increasing the internal pressure on the fluid inside the liner. This increased pressure could cause fluid to be pushed out through the suction tube toward the patient or otherwise out the collection tube. Fluid may also be pushed out the port for the tandem tube toward a secondary canister. When the interconnected canisters are disconnected, fluid may be ejected from the tandem tube, thereby possibly contaminating surfaces or personnel.

As a further result of the increased liner pressure differential, the canister liner may still be sufficiently enlarged or inflated to remain in contact with the walls of the canister. To remove the lid and liner, personnel often try to manipulate the lid and liner either by grasping the liner or grasping fittings on the lid to gain an advantage in forcibly removing the lid and liner from the canister. Such manipulation often puts pressure on the liner thereby increasing the tendency of the liner to eject fluid, and also places force on the fittings which could cause removal of caps on fittings or breakage of fittings, connections or caps. Each of these could cause contamination through ejection of fluids.

As long as vacuum is applied to the system, steady state exists throughout the system. However, once vacuum is removed or once vacuum is removed and personnel attempt to dismantle the system to dispose of the filled liners, the possibility of contamination increases. There exists, therefore, a need for a system which further minimizes the possibility of loss of fluid or contamination in vacuum collection systems.

SUMMARY OF THE INVENTION

The present invention provides a fluid collection system which minimizes the possibility of contamination through fluid reflux of collected fluids, which simplifies assembly of fluid collection systems, improves the integrity of individual fluid collection canisters in a system, and which improves the breakdown procedure for dismantling vacuum canister fluid collection systems for disposal. In accordance with the present invention, a fluid collection system includes a fluid collection reservoir, a cover and a liner within the reservoir comprising an enlargable or expandable wall portion such that the wall portion may expand if the liner fills with fluid. Such a fluid collection system makes a significant use of the pre-existing configuration of a suction canister system, especially a system which has at least one of the canisters filled with fluid, by taking advantage of the pressure characteristics of such a system, both while the vacuum is applied and after vacuum is removed. For example, after a particular liner has become filled, the liner is distended even more than the amount it is distended during filling, caused by the change of pressure inside the liner resulting from the blocking of the vacuum in the vacuum port by the float valve, assuming the collection tube is open. Then the possibility of reflux increases when the vacuum from the vacuum source is removed, because of the release of the distended liner (such as by removing the vacuum pump or breaking the seal on the lid). The inherent elasticity of conventional liners maintains that pressure differential, when the seal between the lid and the canister is broken and the lid and liner combination removed. By contrast the new liner is allowed to expand, preferably outward of the canister, while still retaining the contained fluid, thereby reducing the pressure differential between the fluid and atmospheric to approximately zero. Thereafter, the fluid inside the liner is no longer "pressurized" and can be handled in accordance with standard procedures. In one particularly beneficial form of the invention, the enlargable or expandable wall portion of the liner is formed from bellows or accordion-type folds or pleats or a single fold or extendable undulation formed in the liner adjacent the cover, so that a given fold extends circumferentially around the liner. Preferably, multiple folds are similarly arranged and distributed with respect to each other axially so that the lid can move upward away from the bottom of the liner as the liner expands. A single undulation may be preferred for quality control purposes, because making or forming multiple pleats sometimes may result in stretching of a portion of the wall of a given pleat or fold.

In a further preferred form of the invention, the seal between the canister and the lid is formed such that the seal is maintained while vacuum is applied between the canister wall and the liner but whereby the connection between the lid and the canister is broken when the liner is full and the vacuum removed, thereby lifting the lid off of the canister and the liner to expand to decrease the pressure differential between the liner and atmosphere.

In one preferred embodiment, the folds or pleats are formed so as to permit approximately one-fifth again as much volume to be created in the liner as the folds expand, compared to its unexpanded volume. Such an arrangement accounts for any additional volume of fluid which might otherwise be expelled in conventional liners due to the pressure differential, as well as any additional material which may be added to the liner for treating its contents.

In another form of the present inventions, a fluid suction canister system is provided with a one-way valve in the port for the fluid coming into the canister so as to allow fluid into the canister but to prevent fluid from exiting the canister through the port. Such a one-way valve would prevent reflux, of fluid in the tube, along the collection tube as well as preventing reflux of fluid out of the liner through the port. In one preferred embodiment, the valve is a flapper valve.

In a further form of the inventions, a fluid collection system is provided which includes first and second fluid collection reservoirs, a fluid conduit connecting the first and second reservoirs and a one-way valve in the conduit for allowing fluid flow in the conduit, for example when the conduit is attached, and preventing fluid flow out of the conduit when the conduit is removed from one of the reservoirs. Such an arrangement is particularly suited to the tandem tube, so that no fluid is lost from the tandem tube when it is disconnected from one of the canisters. In the preferred embodiment, the tandem tube is to be removed from the downstream canister, and the valve is placed in the tandem tube at the connector for the downstream canister. In a further preferred embodiment, the input of the downstream canister also has a one-way valve, such as that described above, in the lid of the canister. In a still further preferred embodiment of the invention, the opposite end of the tandem tube is non-removable from the first canister so that the tandem tube cannot be removed inadvertently from that canister, and so that a tandem tube remains with a full liner, to be properly disposed. Alternatively, the tandem tube can include valves at each end of the tube. In a still further preferred form of the invention, the valve at the end of the tandem tube is held open when it is connected to the downstream canister and closes to seal the tandem tube as the tandem tube is being removed for the downstream canister.

In another form of the inventions, a female connector is provided having a sealing element wherein the connector attaches to a male connector portion having a cross-sectional configuration conforming to a portion of the sealing element. The connector includes a connector housing, a female mating portion in the housing having a wall defining an opening for accepting the corresponding male connector portion and wherein the wall begins at an entrance to the connector and terminates at an end wall. A flexible wiper seal is provided internal to the entrance to the connector and includes a wall defining an opening smaller than the dimension of the female portion for engaging and preferably conforming to the outside wall of the male portion when the female portion and the male portion are mated. This connector is particularly suited to the tandem tube connector for the connection with the downstream canister. The flexible wiper seal preferably is formed from a rubber or other flexible material having an opening or cut (such as a single cut or "X"-cut) smaller than the male portion so that the wiper seal contacts and slides along the surface of the male connector portion to minimize the possibility of leaving fluid on the male connector portion, since the male connector portion is exposed after the tandem tube is removed, and prior to being capped.

In another form of the inventions, a non-removable connector is provided for connecting a first element, such as the tandem tube, to a second element, such as the outlet port in the upstream canister lid. The port has a wall defining an opening in the second element into which the connector is to be mounted, wherein the wall includes an external opening and a known length toward the opposite end of the wall from the opening. The connector has a body which includes a proximal stop surface for limiting the distance the connector can pass into the opening. A plurality of legs extend distal of the stop surface to pass into and through the opening when the connector is connected to the second element. Outwardly extending catches are formed on a plurality of the legs having proximately facing ramp surfaces, such that when the connector is engaged in the opening and a withdrawing force is applied to the connector, the ramps engage the end wall and so that the legs are cammed inwardly into the opening until at least two of the legs contact each other to prevent further withdrawal of the connector. This connector is particularly suited to the tandem tube where it is desired to keep the upstream end of the tandem tube permanently connected to the lid of the upstream canister. In one preferred form of the invention, the mating portion of the connector includes four evenly and circularly distributed legs extending into the opening of the tandem port on the upstream canister. The outwardly extending catch on each leg engages the end wall to keep the connector from being removed. However, since the legs can be moved inwardly toward each other relative to the wall of the opening, the proximally facing ramp surfaces on the first two oppositely disposed legs are cammed inwardly if a removing force is applied to the connector such that the connector moves slightly outwardly relative to the port. By the camming action, the first two oppositely facing legs move inwardly toward each other and, preferably, contact, while still engaging the wall. While in contact, the adjacent second pair of legs cannot move inwardly sufficiently enough to disengage from the wall. As a result, all four outwardly extending catches remain engaged with the wall, preventing removal of the connector from the port. In a further preferred embodiment, the catches on the first, ramped legs extend outwardly somewhat further than the catches on the second legs.

It is therefore an object of the present invention to provide an improved vacuum canister fluid collection system which further minimizes the possibility of contamination by collected fluids.

It is a further object of the present invention to take advantage of the inherent pressure characteristics of preexisting systems to improve the integrity of the system and of the individual fluid collection canisters and their components.

It is another object of the present invention to provide a vacuum canister fluid collection system having a liner with an enlargeable or expandable wall portion to decrease any possible pressure differential within the liner after vacuum is removed from the system.

It is a still further object of the present invention to provide a vacuum canister fluid collection system which minimizes the possibility of reflux or ejection of collected fluids during and after disassembly of the system.

These and other objects of the present inventions will be demonstrated by the drawings and the detailed description of the preferred embodiments, which follow.

BRIEF DESCRIPTION OF THE DRAWINGS

FIG. 3 is a top plan view of a lid for use with a canister such as shown in FIG. 2.

FIG. 4 is a partial vertical section of the lid of FIG. 3 taken along lines 4—4 showing the vacuum port and patient port.

FIG. 4A is a partial section of a portion of the lid showing a closure clip or bump for the lid.

FIG. 5 is a cross-section of a patient valve with the lid in accordance with one aspect of the present invention.

FIG. 12 is a tandem tube valve in place on the patient port of a downstream canister with the flapper valve held open by the patient port on the downstream lid.

FIG. 13 is a cross-sectional view similar to that of FIG. 12 showing the tandem tube partially removed from the patient port and showing the flapper valve partially closed and the wiper valve contacting the wall of the port.

FIG. 14 is a cross-sectional view of the tandem tube valve similar to that of FIG. 12 with the valve being further removed and the wiper valve in contact with the mating port.

DETAILED DESCRIPTION OF THE PREFERRED EMBODIMENTS

In accordance with the present invention, a fluid collection system is provided which takes full advantage of pressure differentials created in the fluid collection system to increase the integrity of the system and its component parts, and to reduce the possibility of contamination through fluid loss or reflux. The system of the present invention provides a more secure system and provides lid and liner combinations which are more easily neutralized and disposed of.

Figure 1:
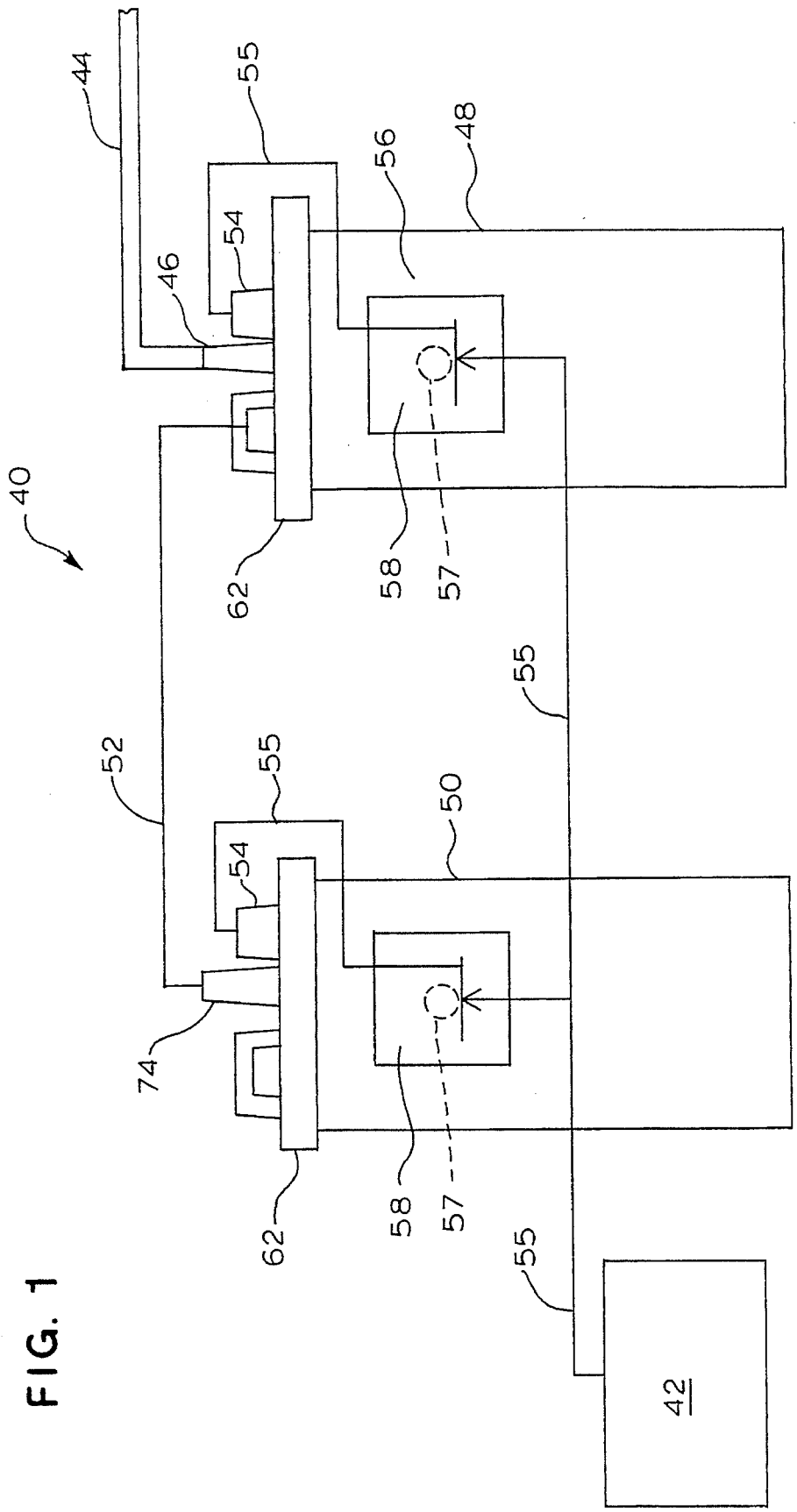
FIG. 1 is a schematic and side elevation view of a vacuum canister fluid collection system for use with the present invention.

In accordance with the present invention, a vacuum canister fluid collection system 40 (FIGS. 1 and 2), such as may be used for collecting fluids from patients or other sources during operations, medical procedures or other uses, includes a conventional vacuum source such as pump 42 and a collection tube 44 for collecting fluid from the patient or other source. The collection tube is coupled to the patient port 46 in a first vacuum canister 48, described more fully below. The first canister 48 is fluidly coupled to a second canister 50 through a tandem tube 52. The vacuum pump 42 is coupled to vacuum ports 54 on the first canister 48 and on the second canister 50 through conventional hoses 55 for providing the required pressure differential, as is known to those skilled in the art. Additional suction canisters may be provided as necessary.

In the preferred embodiment, vacuum is also applied to the canister through the canister wall 56 through a wall opening 57 by a vacuum attachment 58 mounted to the outside of the canister wall. Such a configuration is commonly used with the Baxter Medi-Vac CRD flex canister system whereby vacuum is applied from the attachment 58 to the canister through the opening 57 and also to the interior of the liner through the vacuum port 54.

Figure 19:
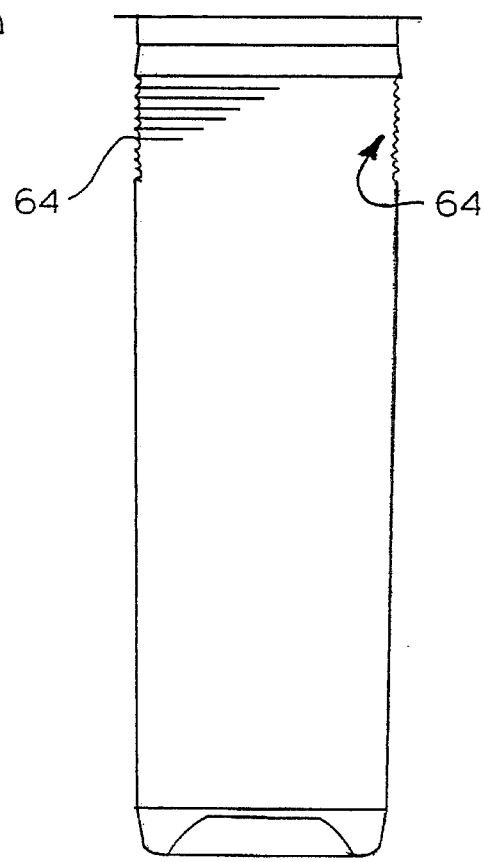
FIG. 19 is a cross-sectional view of a pleated molded liner for a canister in accordance with the present invention.

Each canister includes a flexible liner 60 (FIG. 2) fixedly and fluidly sealed within a circular groove formed in the bottom of the lid 62 so that the lid and the liner form a complete and closed container, except for the ports described more fully below. The liner preferably includes an enlargeable or expandable wall portion 64 (FIG. 19) which can expand if the liner fills with fluid, such that the effective internal volume of the liner increases. With this configuration, the liner with an unexpanded but expandable section preferably forms the standard volume for receiving fluid, for a given canister size. If the liner fills with fluid to the standard full volume, the expandable portion 64 can then expand to effectively increase the total volume of the liner. The increased volume preferably reduces any differential pressure between the interior of the lining and ambient pressure when vacuum is removed from the system. The increased liner volume also permits addition of other fluids or materials, such as treatment agents like Isolizer for the fluid.

In the preferred embodiment, the expandable wall portion is formed from one or a series of pleats or bellows. Preferably, each pleat is formed circumferentially around the entire circumference of the liner at a location near or adjacent the lid (see FIG. 2). The series of pleats are preferably formed axially with respect to each other so that the wall portion of the liner can expand or enlarge axially or longitudinally or both to relieve any pressure differential that may exist when the vacuum is removed. Circumferential pleats are preferred over longitudinal pleats because longitudinal pleats may expand even while vacuum is present in the canister and may make it more difficult to remove the liner from the canister. If longitudinal pleats are used, it is preferred to also use circumferential pleats.

In the preferred embodiment, for a 3000 ml canister, the enlargeable wall portion may permit addition of 400–600 mls of volume to the liner. It has been found that the pressure differential of conventional liners could result in reflux of approximately 250 ml of fluid at maximum vacuum. By providing about one-fifth or one-sixth again as much additional volume, the additional liner volume may relieve or reduce the pressure differential, as well as accommodate addition of materials for solidifying or otherwise neutralizing the fluid.

Preferably, the pleats are uniform and extend completely around the circumference of the liner, for each pleat. The pleats preferably have a wave length of approximately 0.166 inch, each crest having a preferred radius of approximately 0.015 inch and each trough, extending inward relative to the liner, having a preferred radius of approximately 0.030 inch for a typical preferred liner wall thickness of 0.010 inch. In another embodiment, a single fold or undulation may be used to avoid thinning of walls of parts of a pleat or fold which may develop during molding of the bag.

Figure 2:
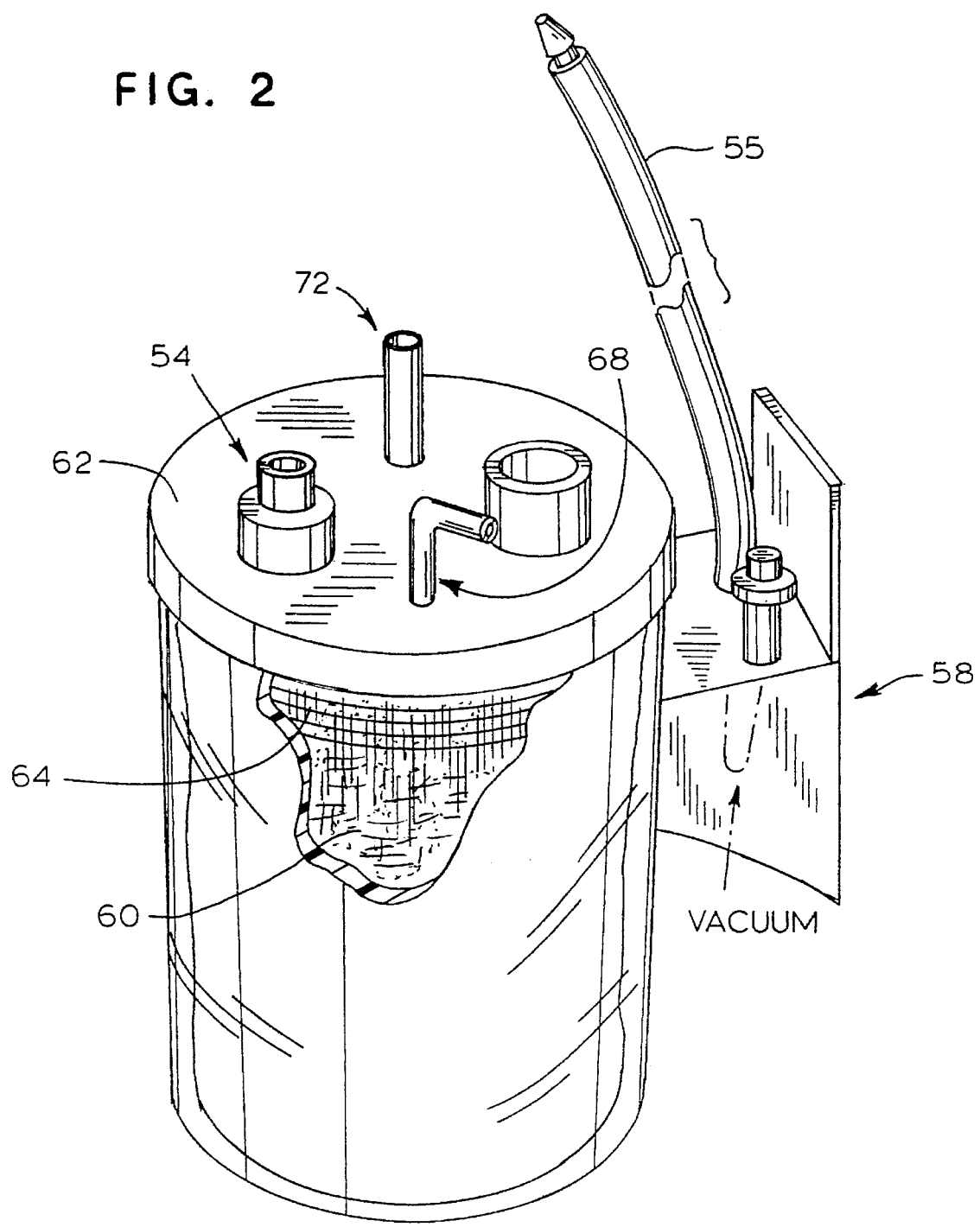
FIG. 2 is a perspective and partial cutaway view of a canister for use with the fluid collection system of the present invention.
Figure 6:
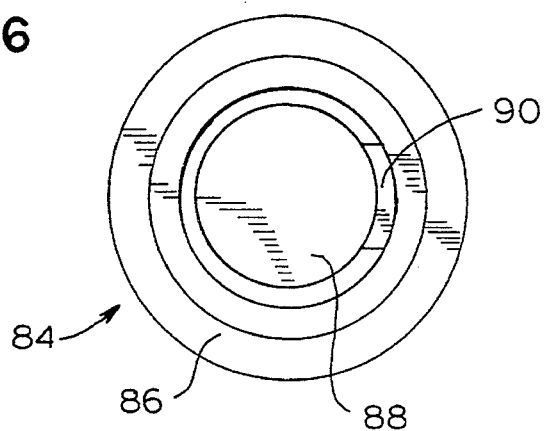
FIG. 6 is a plan view of a flapper valve for use with the patient port.
Figure 7:
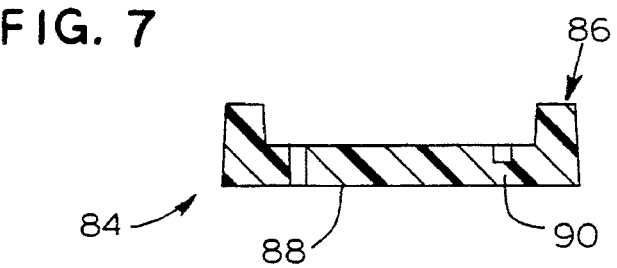
FIG. 7 is a cross-sectional view of the lid flapper valve of FIG. 6.
Figure 8:
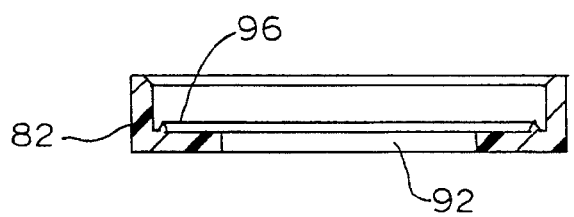
FIG. 8 is a cross-sectional view of a retainer for the lid flapper valve of FIG. 6.

In operation, vacuum is applied to the cavity or spacing between the canister wall and the liner, and the lid is held in place on the rim of the canister to form an appropriate seal, as is known to those skilled in the art. With the evacuation of the cavity between the liner and the canister walls, the wall of the liner expands flexibly outward toward the canister wall to provide a portion of the vacuum for suction and to preclude collapse of the liner wall, as is also known to those skilled in the art. The vacuum system pulls fluid into the interior of the liner through the patient port 46 (FIGS. 3 and 4) and into the volume defined by the liner (FIG. 2). When the liner is full, a conventional float valve 70 (FIG. 4) attached to the bottom of the vacuum port 54 closes, removing vacuum to the interior of the liner from that port. Thereafter, continued suction results from vacuum applied to the liner in the second canister, which then brings fluid from the liner in the first canister out through the tandem port 72 through the tandem tube 52 and into the liner of the second vacuum canister 50 (FIG. 1) through its respective patient port 74.

When the operation or procedure is complete, the tandem tube is removed from the second canister 50, the vacuum tube is removed from the vacuum port on the lid 62, and also from the vacuum attachment 58. The vacuum port and the other ports on tile lid 62 are capped (not shown), as is the free end of the tandem tube. By turning off the vacuum, the pressure between the liner and the canister walls approaches ambient pressure. Because of the earlier vacuum, and influx of fluid into tile liner, the fluid pressure within the liner exceeds ambient pressure. This resulting pressure differential exerts an expansive force on the liner and lid. Any expansive forces in the radial or downward direction are retained or contained by the canister wall and bottom surface. However, the only element containing the pressure against the lid is any seal or interference snap fit which may exist between the lid and the rim of the canister after vacuum is removed. The pressure differential is sufficient to break the lid-rim connection, and the internal fluid pressure within the liner presses against the lid and creates a force expanding the pleats, with a resultant increase in liner volume, which is accommodated by movement of the lid upward away from the rim of the canister. Expansion continues until the internal pressure of the fluid is counterbalanced by the return force provided by the flexible material of the liner. It has been found that the internal liner pressure is sufficient, after removal of the vacuum, to force the lid off of the rim of the canister to allow the liner to continue to expand upwardly. It has also been found that the conventional lid design was sufficient to permit the lid to lift off of the rim, without redesign. However, it was also found that the five clips or bumps 75 (FIGS. 3 and 4), evenly distributed about the internal circumferential wall of the lid, were better positioned downward, because repeated flexing of the original lid with vacuum may cause the clips to gradually walk up the rim of the canister. The clips were also enhanced to give more of a snap action.

In the preferred embodiment, the patient port 46 on the lid 62 is preferably enlarged to be approximately the same size as the preexisting "ortho" port used with orthopaedic surgical applications. The patient port well 76 is also enlarged to accommodate the larger port cone or riser and connectors, as necessary. The patient port riser may accommodate elbow adaptors (such as is shown in FIG. 2) and other connectors, as is known to those skilled in the art.

The patient port, in accordance with a further aspect of the present invention, includes a one-way valve 78 (FIGS. 5–8) mounted to the underside of the lid 62 to allow fluid into the liner and to prevent fluid from exiting the liner through the patient port.

As shown in FIG. 5, the patient port is slightly tapered to a narrower opening for accepting the collection tube 44, in the case of the first collection canister, or for accepting the tandem tube valve in the case of the second or other vacuum canisters. A circular wall 80 surrounds the patient port and extends downwardly from the underside of the lid to the interior of the liner for accepting, on the outside thereof, a flapper valve retainer 82 (FIG. 8) and for accepting, within the interior thereof, a flapper valve 84. The flapper valve (FIGS. 6 and 7) is preferably a unitary polyisoprene material having an outer ring 86 surrounding an inner moveable valve element 88 substantially in the shape of a circle except for a web 90 connecting the valve element 88 to the outer ring 86. The outer dimension of the valve element 88 is less than the inner dimension of the outer ring 86 so as to form a space for permitting movement of the valve element and fluid flow through the outer ring 86.

The flapper valve retainer 82 (FIG. 8) is preferably cup-shaped with a circular opening 92 through which the valve element 88 can extend to permit fluid flow through the flapper valve and into the interior of the liner. The retainer 82 fits over and around the downwardly extending wall 80 (FIG. 5). The fit is facilitated by a chamfer. The radial portion of the retainer includes an energy director ring 96 extending upwardly toward the circular wall 80.

The flapper valve prevents reflux of fluid from the interior of the liner along the passageway of the collection tube 44. Additionally, the flapper valve inhibits fluid flow through the collection tube when the valve is closed, such as after the vacuum has been removed. As a result, reflux of fluid from the open end of the collection tube is minimized. The wider patient port permits use of the fluid collection system in orthopaedic as well as other surgical and medical uses without having to go to another system. The larger port permits easy passage of particulate material which may be passing through the collection tube 44.

In the preferred embodiment, the internal side of the patient port includes an annular groove 98 having an inside wall equal to or slightly smaller than the outer dimension of the moveable valve element 88, to ensure proper seating of the valve element against its seat.

In the use of a single suction canister, the tandem port is securely capped to prevent any fluid leakage out the tandem port. What was conventionally the orthopaedic port has been modified to form the tandem port, having a shorter tapered cone or riser than was ordinarily used with the orthopaedic port but tapered in the other direction than the prior "ortho" port. The inside diameter of the port is slightly larger to accept the tandem connector, when used, to fix the tandem tube 52 to the lid. The opposite end of the tandem tube includes the tandem valve, described more fully below.

Figure 9:
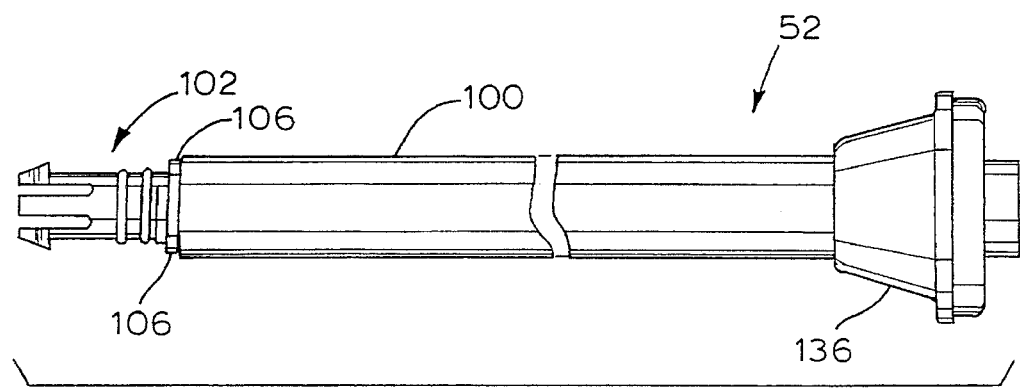
FIG. 9 is a tandem tube in accordance with a further aspect of the present invention.
Figure 10:
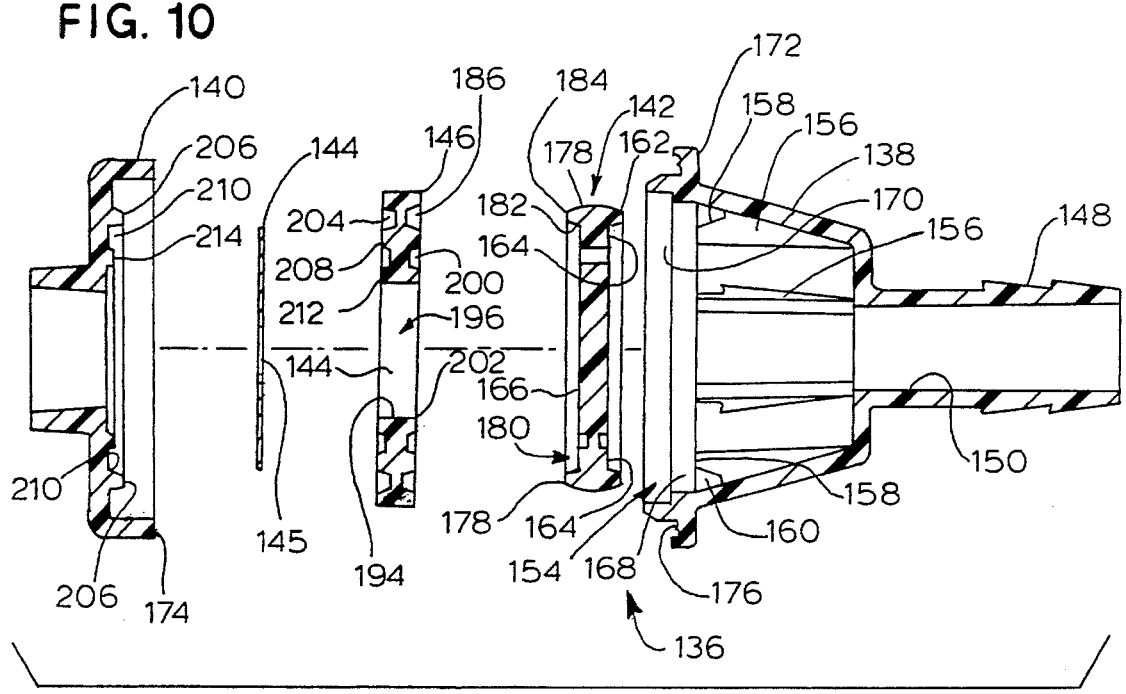
FIG. 10 is a longitudinal cross-section of a tandem tube valve in an exploded configuration.
Figure 15:
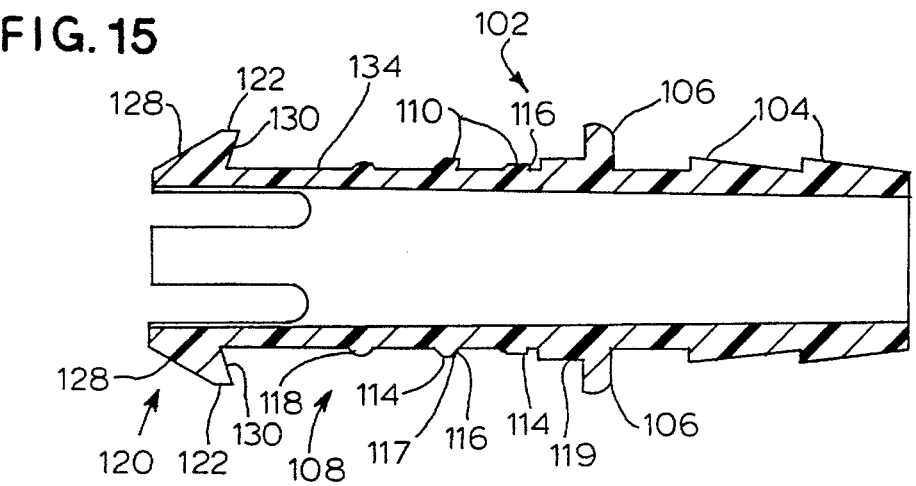
FIG. 15 is a longitudinal cross-section of a tandem tube connector.
Figure 16:
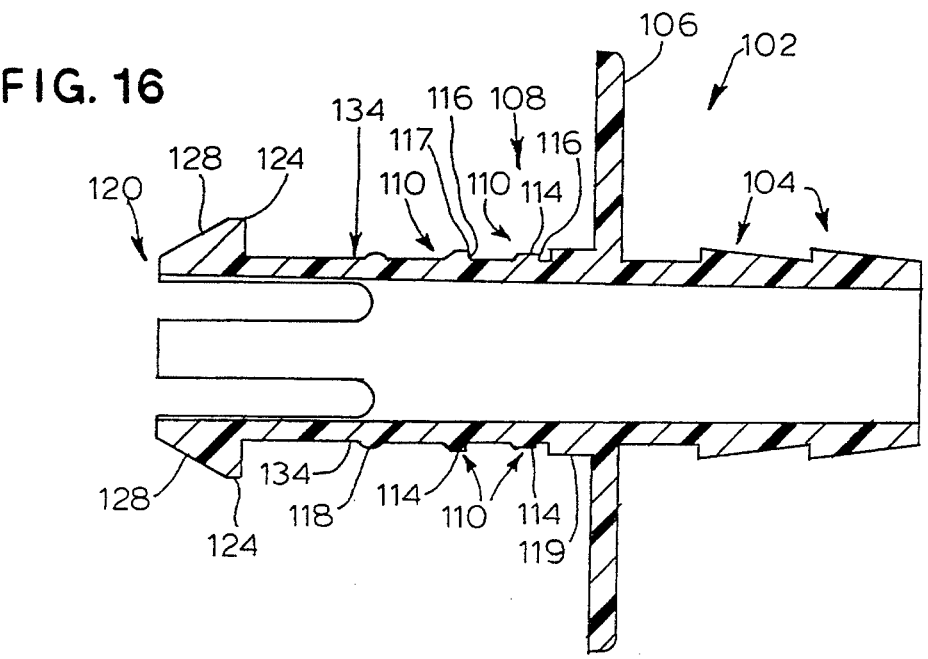
FIG. 16 is a further cross-section of the tandem tube connector rotated about a longitudinal axis approximately 90 degrees from the view shown in FIG. 16.
Figure 17:
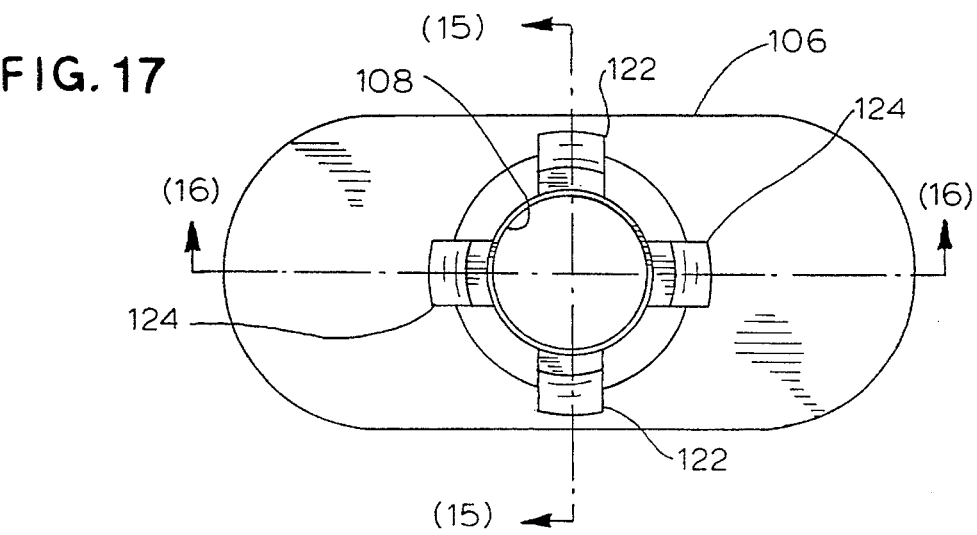
FIG. 17 is a bottom plan view of the tandem tube connector.

The tandem tube 52 (FIG. 9) includes a flexible tube 100 mounted to the tandem connector 102 through an interference fit over ribs 104 (FIGS. 15 and 16). The interference fit is sufficient to prevent removal of the tube from the connector by hand. The tandem connector 102 includes wings 106 to serve as a stop to prevent the connector from being inserted into the tandem port further than the stop and also to provide a surface for applying pressure on the connector to press it into the tandem port. The tandem tube connector has a body 108 preferably cylindrical in general outline with one or more circumferential ridges or coupler rings 110 to form a seal between the tandem connector body and the interior wall of the tandem port when the connector is fully seated in the port. The lower or distal portion of each ring 110 slants upwardly and outwardly from the body to a flat circumferential wall 114 which engages the interior wall of the port. Each ring terminates at a flat surface 116 extending from the circumferential wall 114 back to the body 108. The distal-most ring includes an outwardly extending sealing shoulder 117 extending circumferentially around the proximal-most portion of the wall 114. Below the lower-most ring 110, a semicircular ring 118 is included for centering the connector in the port, as is the cylindrical surface 119.

Figure 18:
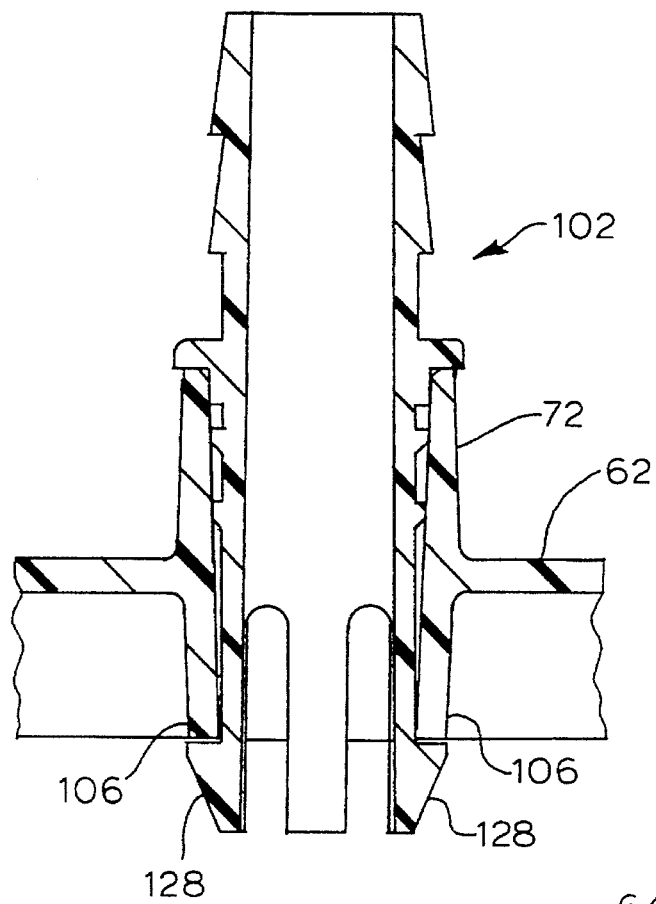
FIG. 18 is a cross-sectional view of the tandem tube connector attached to a canister lid through a tandem tube port.

The distal or innermost portion of the tandem connector body 108 terminates in a plurality of legs 120 for passing through the tandem port when the connector is connected to the tandem port. Preferably, four equally, circumferentially spaced legs are positioned around and form the inside terminal end of the tandem connector. Each leg has a preferably uniform wall thickness except for outwardly extending catches or locks, the first two of which locks 122 are shown in FIG. 15 on the first pair of legs and the second two of which locks 124 are shown in FIG. 16 on the second pair of legs. The locks 122 and 124 extend outwardly to engage the innermost chamfered (at about 10°) rim of the tandem port, which rim 106 extends downwardly from the underside of the lid 62 (FIG. 18). The 10° chamfer focuses the bending at the intersection of the lock with the leg. Each lock includes a guide surface 128 for pushing the legs inward through the action of the passageway of the tandem port when the tandem connector is first inserted into the tandem port. Each guide 128 terminates in a radially inwardly extending locking surface. The locking surface for the first ramp locks 122 are ramping or camming surfaces 130 extending radially inwardly and downwardly toward the body of the tandem connector. The locking surfaces for the straight locks 124 extend straight radially inwardly toward the tandem connector body.

Once installed, the tandem connector 102 is effectively fixed in the tandem port. If any removal force is applied to the tandem tube or its connector, the camming surfaces 130 will bear against the lower rim of the tandem port, thereby camming the corresponding first pair of legs 120 inwardly until the two legs in the pair meet. Because of the angled surfaces 130, the first pair of legs 120 are bent inwardly before the second pair of legs 120 begin to bend inwardly through any action of the rim of the tandem port. Moreover, any bending of the second pair of legs 120 will cause them to contact the other pair of legs, preventing any further inward bending of the legs. The ramped locks 122 are dimensioned so that the outer edges of the ramped locks will still engage the rim of the tandem port even when the innermost points of the first pair of legs 120 would be touching along the center line, because of bending at the bending points 134. Additionally, the guides 128 for the straight locks 124 are dimensioned so that they still engage the rim of the tandem port even when they are bent inwardly to contact the first pair of legs. As a result, no amount of force will unlock the legs from the rim of the tandem port, without destroying the connector itself. It should be noted that the connector can still be inserted into the tandem port and locked since the bending upon such insertion takes place at the point where the legs join the rest of the tandem connector body 108 rather than solely at the point where the ramped locks 122 and straight locks 124 join the connector legs.

In the preferred embodiment, a tandem tube connector having an internal diameter at the legs of approximately 0.323 inches and an internal diameter at the opposite end of approximately 0.290 inches has a thickness for the legs of approximately 0.400 inches and an outside diameter at the points of the ramped locks 122 of 0.573 inches and an outside diameter at the straight locks 124 of approximately 0.543 inches. The distance from the distal side of the rim 106 to the proximal-most point on the ramped locks 122 is preferably about 0.790, which is the same as the distance to the proximally-facing surfaces on the straight locks. Tolerances should be made to ensure proper seal between the tandem connector body and the port while still allowing the movement of the legs to maintain a stable lock. An alternative lock has the body extend completely to the end of the locking elements (to form a complete cylinder) and reducing the radial size of the locks while still ensuring a stable lock and easy installation of the connector in the port while ensuring a proper seal.

The tandem tube valve 136 (FIGS. 10–14) permits two way fluid flow through the tandem tube when the tandem tube valve 136 is mounted to a patient port on a canister, but prevents fluid flow out of the valve when the valve is disconnected. The tandem tube valve substantially minimizes the possibility of contamination when tandem-connected canisters are disconnected, and while any given liner-lid combination is being disposed. The tandem valve is preferably placed in the portion of the tandem tube which is to be connected to a secondary canister since the habit of most technicians is to disconnect tandem tubes from the secondary canisters rather than from the primary canister. However, it should be understood that suitable valves can be placed at either end of the tandem tube to achieve the same purpose, especially if both ends of the tandem tube can be disconnected from their respective ports.

The tandem valve preferably includes a tandem valve housing top 138 and a bottom 140. The housing positions and retains a flapper valve 142 and a wiper valve 144, the wiper valve having a wall 145 defining an opening for the riser portion of the patient port, separated by a valve spacer 146. These elements will be described more fully below.

Figure 11:
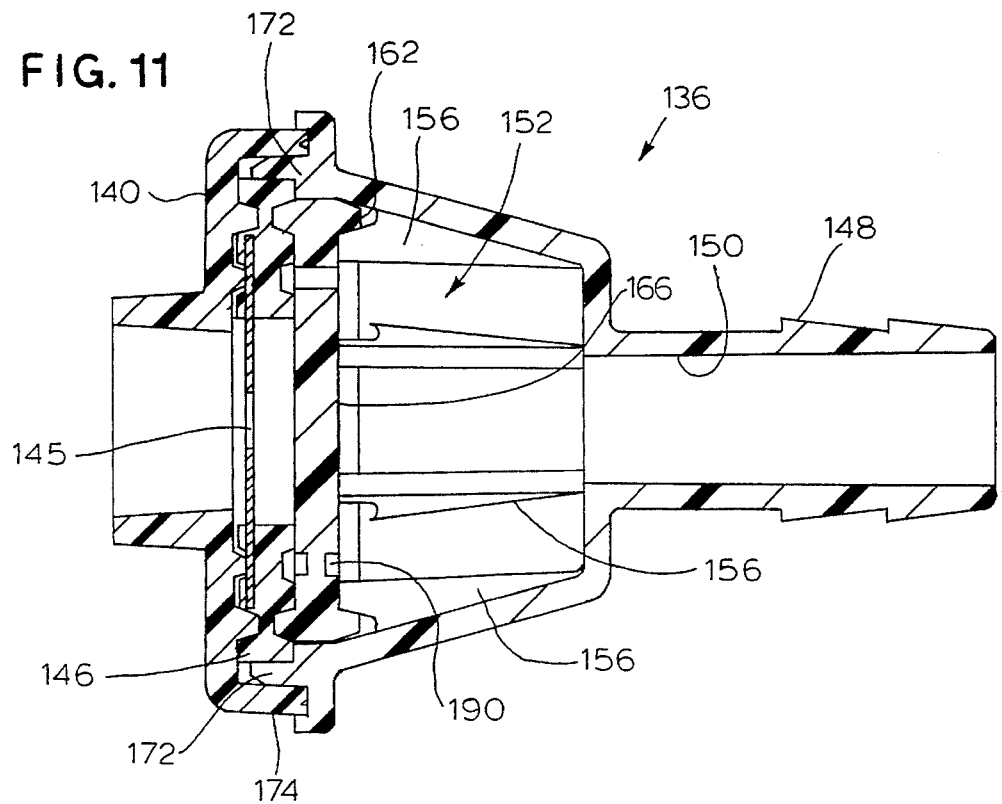
FIG. 11 is a cross-sectional view of the tandem tube valve of FIG. 10 in assembled form.

The housing top 138 includes one or more ribs 148 for frictionally engaging the end of the tandem tube 100. The ribbed portion of the housing defines a passageway 150 through which fluid may pass from the tandem tube into the secondary canister. The passageway terminates in the interior 152 of the housing top 138. In longitudinal cross-section, the interior 152 of the housing is substantially trapezoidal in shape with the narrower portion adjacent the passageway 150 and the wider portion at an opening 154. A plurality of supporting ribs 156, preferably eight, are uniformly distributed around the inside circumference of the trapezoidal housing portion and diverge slightly from the narrow portion of the housing to the opening 154. The ends 158 of the supporting ribs are spaced from the adjacent wall to form recesses 160 for receiving an outer circumferential wall 162 on the flapper valve 142 (FIG. 11). The spaced ends 158 engage a support surface 164 on the flapper valve, interior to the wall 162 and exterior to the moveable valve element 166 of the flapper valve. The trapezoidal housing portion provides sufficient space for the moveable valve element 166 to move into the housing to permit fluid flow past the flapper valve from the tandem tube into the secondary canister.

The flapper valve fits within a bore 168 in the opening 154 and is held in place by the spacer 146 (FIG. 11). The wiper valve 144 is preferably an apertured, disc-shaped sheet of rubber or similar material and fits against the opposite side of the spacer 146 and is sandwiched in place by the bottom portion 140 of the tandem valve housing.

The spacer 146 fits into a counterbore 170 in the opening 154 of the top housing. The counterbore 170 is formed in an end wall 172 of the top housing and held in place by the bottom housing portion 140. The bottom housing has an outer circumferential wall 174 which engages a circular channel 176 formed around the end wall 172 so that the top and bottom housing portions may be welded or otherwise bonded and sealed.

The flapper valve 142 is preferably substantially symmetrical about a plane intersecting the central axis of the flapper valve thereby forming a plane to which the central axis is normal. The wall portion 162 is part of a short cylindrical outer wall 178 surrounding a ring portion 180. The supporting surface 164 on one side of the ring portion 180 engages the ends 158 on the ribs 156. On the opposite side, surface 182 and surface 184 engage mating grooved portions 186 of the spacer 146. Flapper valve 142 is thereby sandwiched between the spacer 146 and the top housing 138.

The moveable valve element 166 is coupled to and supported by the ring portion 180 by two secondary webs (not shown) spaced 120° apart, on each side and equidistant from a primary web 190.

Spacer 146 (FIG. 10) is also preferably symmetrical about a plane to which the center axis of the spacer is normal. The spacer preferably has a wall 194 defining an opening 196 through which the cone or riser of the patient port of the secondary canister is inserted to engage and open the moveable valve element 166 of the flapper valve in the valve housing. On the flapper valve side of the spacer, an inner groove 200 as well as the wall 194 define the valve seat 202 against which the valve element 166 seats when the tandem tube valve is removed from the mating port.

On the wiper valve side of the spacer, the spacer again has a first outer groove 204 for engaging a corresponding circular ridge 206 in the inside of the bottom housing 140. The inward adjacent circular ridge 208 on the spacer 146 engages the groove 210 to sandwich the wiper valve 144 between circular ridge 212 on the spacer and circular ridge 214 on the bottom housing. Preferably, the groove 210 and the corresponding ridge 208 also capture part of the wiper valve to hold it in place.

FIGS. 12–14 demonstrate the operation of the tandem valve as the valve is being installed on the port. In FIG. 12,
the tandem valve and connection is fully seated on its corresponding patient port 46 so that the riser of the patient port holds the moveable valve element 166 of the flapper valve open, permitting fluid flow from the tandem tube into the canister in accordance with the proper pressure differential. Additionally, the opening 145 in the wiper valve 144 elastically surrounds the riser. (While FIGS. 12–14 show the wiper valve to be somewhat rigid, it should be understood that the wiper valve is flexible, as natural rubber would be.) In FIG. 13, the tandem valve is partially installed on its corresponding riser and the moveable valve element 166 of the flapper valve is pushed ahead of the top of the riser as the riser enters the tandem valve housing. FIG. 14 shows the valve only partly in place on the riser, with the wiper valve partly deflected. Removal of the valve from the port follows a reverse process. In the transition between FIGS. 12 and 13, upon removal, it is believed that the wiper valve begins to bend or flex downwardly, following the riser. Eventually, the wiper valve will become inverted downwardly. Thereafter, the opening 145 in the wiper valve 144 slides along the riser as the riser is removed, wiping any fluid in front of it. Finally, the moveable valve element of the flapper valve is seated on the valve seat 202 and the wiper valve is almost completely removed from the riser.

With the tandem valve, further flow of fluid from the tandem tube outward of the tandem valve is prevented once the tandem tube is disconnected from its associated tandem port. Any fluid within the tube is retained therein or falls back into its primary canister. The valve operates regardless of whether or not removal of the tandem tube valve is intentional or accidental.

A tandem tube valve cap (not shown) is retained on the tandem tube so that the opening on the tandem tube valve housing can be capped at any time. After being capped, the tandem tube is fully sealed between the cap and the liner of the lid-liner combination to which the tandem tube is connected.

In the preferred embodiment, the canister lid, connectors and ports are formed from high density polyethylene. The liner is preferably formed from ultra low density linear polyethylene and the tandem tube connector is preferably formed from a polypropylene homopolymer. The port caps such as the tandem tube valve cap are preferably formed from low density polyethylene. The valve housing is preferably formed from styrene, as is the tandem valve spacer, while the flapper valve is preferably formed from natural or synthetic polyisoprene and the wiper valve is preferably formed from natural pure gum rubber. The opening 145 in the wiper valve 144 is preferably 0.125 inch for a minimum outside patient port diameter of 0.361 inch.

A vacuum canister fluid collection system and its components have been described and which will minimize the possibility of reflux or loss of fluid upon removal of vacuum, thereby minimizing the possibility of contamination or injury. Additionally, the possibility of contamination through accidental removal of caps on ports or loss of vacuum is also minimized. The system is designed so that full canisters will have their lids unsealed and disengaged from the canister upon removal of vacuum to minimize any possible pressure differential between the liner and atmospheric pressure. Preexisting pressure differentials and components are beneficially used to accomplish this result.

Although the present invention has been described in detail with reference only to the presently preferred embodiments, it will be appreciated by those of ordinary skill in the art that various modifications can be made without departing from the spirit of the invention. Accordingly, the invention is limited only by the following claims.

What is claimed is:

1. A fluid collection system comprising:
   a fluid collection reservoir;
   a cover for the reservoir; and
   a liner within the reservoir having a longitudinal length extending from an upper liner portion to a lower liner portion and comprising a substantially longitudinally nonexpandable sidewall portion that remains substantially unexpanded when the liner is filled with fluid and wherein the nonexpandable sidewall portion has a length, extending in the same direction as the liner length, which is less than the longitudinal length of the liner and which is substantially the same before and after the liner fills with fluid, and further comprising a substantially longitudinally expandable sidewall portion that may expand if the liner fills with fluid and having a length before the liner fills with fluid that is less than an expanded length after the liner fills with fluid.

2. The system of claim 1 wherein the liner includes a surface forming a seal with the cover.

3. The system of claim 1 wherein the liner has an expanded volume and an unexpanded volume, and wherein the substantially expandable sidewall portion of the liner includes at least one circumferentially disposed pleat.

4. The system of claim 3 wherein the fluid collection reservoir includes a bottom and wherein the at least one circumferentially disposed pleat is positioned closer to the cover than to the bottom of the fluid collection reservoir.

5. The system of claim 4 wherein the at least one pleat is permit an expanded volume approximately the size of the unexpanded volume.

6. The system of claim 1 wherein the substantially expandable sidewall portion includes a plurality of circumferential pleats arranged axially relative to one another.

7. The fluid collection system of claim 1 further comprising an inlet port in the cover and a one-way valve for the inlet port for allowing fluid flow into the liner but substantially preventing fluid flow out of the liner.

8. The system of claim 7 wherein the one-way value includes a flapper valve.

9. The system of claim 1 wherein said fluid collection reservoir defines a first fluid collection reservoir, and further comprising a second fluid collection reservoir, having a liner within the second reservoir, and a fluid conduit fluidly connecting the liner of the first fluid collection reservoir with the liner of the second collection reservoir.

10. The system of claim 9 wherein the fluid conduit is locked in place on the cover for the first fluid collection reservoir.

11. The system of claim 9 further comprising a closeable valve between the first and second fluid collection reservoirs.

12. The system of claim 11 wherein the closeable valve is positioned in the fluid conduit between the first and second reservoirs.

13. The system of claim 12 wherein the closeable valve is held open while the fluid conduit is connected between the first and second reservoirs.

14. The system of claim 12 wherein the closeable valve includes a flapper valve.

15. The system of claim 12 further comprising a wiper valve for substantially preventing loss of fluid upon disconnection of the fluid conduit.

16. The system of claim 15 wherein the second fluid collection reservoir includes a connection riser to which the fluid conduit is connected, a connection housing to enclose the connection riser and part of the fluid conduit, wherein the flapper valve and wiper valve are retained within the connection housing, the flapper valve is held open when the housing and riser are connected, and wherein the wiper valve is positioned between the flapper valve and the exposed end of the housing such that, when the fluid conduit is connected to the second fluid collection reservoir, the wiper valve is positioned between the flapper valve and the second fluid collection reservoir.

17. A fluid container system, comprising:
   a rigid container having a sidewall and a bottom defining a first cavity, said container having a wall defining an opening;
   a removable lid, normally covering said opening; and
   a flexible liner located in said first cavity, said flexible liner having a sidewall extending longitudinally and a bottom portion and further having a first relaxed shape wherein the liner sidewall extends to the bottom portion sufficiently so that the bottom portion is adjacent the container bottom portion when said removable lid is covering said opening and so that the bottom portion is longitudinally movable in the bottom of the rigid container, and a second expanded shape extending through said opening when said removable lid is removed.

18. A fluid containment system, as set forth in claim 17, wherein said liner further comprises:
   a bellows portion to allow said liner to expand from said collapsed shape to said expanded shape.

19. The system of claim 17 wherein the rigid container is substantially cylindrical having a substantially circular rim defining the opening and wherein the flexible liner is fluidly and hermetically sealed to the removable lid.

20. The fluid container system of claim 17 wherein the liner has a second expanded shape that provides between approximately 400–600 milliliters of additional volume relative to the first collapsed shape of the liner.

21. The system of claim 18 wherein the bellows portion comprises a plurality of pleats wherein each pleat is oriented circumferentially about the liner and is oriented axially relative to adjacent pleats.

22. The system of claim 21 wherein the expanded shape is at least 1.2 times the volume of the relaxed shape.

23. The system of claim 17 wherein the liner includes an expandable pleated portion to permit expansion of the liner when the liner has become substantially full.

24. A device for collecting fluids, comprising:
   a rigid canister, said canister having sidewalls and a bottom connected to said sidewalls to define a first cavity having a first top opening, said canister having a first vacuum port;
   a flexible liner having a longitudinal length extending from an upper liner portion to a lower liner portion and comprising a substantially longitudinally nonexpandable sidewall portion that remains substantially unexpanded when the liner is filled with fluid and wherein the nonexpandable sidewall portion has a length, extending in the same direction as the liner length, which is less than the longitudinal length of the liner and which is substantially the same before and after the liner fills with fluid, said liner being shaped to generally conform to said first cavity to define a second cavity, said liner having a second top opening, said liner also having expansion means for allowing said liner to expand in a direction toward said top opening and having a length before the liner fills with fluid that is less than an expanded length after the liner fills with fluid;

a lid, said lid being sealed to said second top opening of said liner, and having clip means for releasable sealed engagement with said first top opening of said canister in a configuration to cause said liner to be disposed within said first cavity of said canister when said lid is releasably sealed to said first top opening of said canister, said lid having
- a second vacuum port in fluid communication with said second cavity;
- a fluid intake port;

collection means attached to said fluid intake port for collecting fluid from an outside source;

a first valve in fluid communication with said collection means to prevent fluid from flowing from said second cavity toward said collection means when said second cavity is filled with fluid;

a second valve in fluid communication with said second vacuum port which closes when said second cavity is filled with fluid; suction means for temporarily connecting:
- a first suction through said first vacuum port to said first cavity of said canister when said liner is placed in said first cavity;
  - to cause said lid to be pulled toward said first top opening of said canister to seal said lid against said first top opening, and
  - to subsequently pull said second cavity of said liner against said first cavity of said canister; and
- a second suction through said second vacuum port in said lid to produce suction in said second cavity of said liner which produces suction through fluid inlet port to cause fluid from an outside source to be suctioned into said second cavity,
- whereby when said second suction is disconnected and said first and second valves are closed, said expansion means will cause said second cavity to expand in a direction toward said second top opening to release said lid from said first top opening.

25. A fluid collection system comprising:

a canister defining an inner cavity and having an opening and a bottom;

a lid covering the opening of the canister; and a liner positioned within the inner cavity of the canister, the liner having a volume capacity for receiving collected fluid and having a sidewall extending longitudinally between the lid and the canister bottom, the sidewall of the liner being formed with a substantially longitudinally nonexpandable lower sidewall portion that remains substantially unexpanded when the liner is filled with fluid and wherein the nonexpandable sidewall portion has a length, extending in the same direction as the liner length, which is less than the longitudinal length of the liner and which is substantially the same before and after the liner fills with fluid, and a substantially longitudinally expandable upper sidewall portion having a length before the liner fills with fluid that is less than an unexpanded length after the liner fills with fluid that may expand if the liner fills with fluid to increase the volume capacity of the liner and reduce reflux.

26. The fluid collection system of claim 25 wherein the substantially expandable upper portion of the sidewall portion of the liner includes at least one circumferentially disposed pleat.

27. The fluid collection system of claim 26 wherein the at least one circumferentially disposed pleat has an unexpanded longitudinal dimension of approximately 0.166 inch.

28. The fluid collection system of claim 27 wherein the at least one circumferentially disposed pleat has a crest radius of approximately 0.015 inch and a trough radius extending inward relative to the liner 0.030 inch.

29. The fluid collection system of claim 25 wherein the liner with a volume capacity has a wall thickness of approximately 0.010 inch.

30. The fluid container system of claim 25 wherein the liner has an upper and a lower half and wherein the expandable upper portion is positioned in the upper half of the liner.

31. The fluid container system of claim 30 wherein the upper half of the liner further includes a substantially nonexpandable portion.

* * * * *